United States Patent
Ellingson et al.

(10) Patent No.: US 6,217,556 B1
(45) Date of Patent: *Apr. 17, 2001

(54) DRAINAGE CATHETER

(75) Inventors: Eric Ellingson, Mount Prospect; Greg Groenke, Gurnee, both of IL (US); Grant Clark, Bristol, WI (US); Randy Raine, Mayo, MD (US); Peter Visconti, Chicago, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/044,561

(22) Filed: Mar. 19, 1998

(51) Int. Cl.$^7$ ................................................. A61M 5/178
(52) U.S. Cl. ............................ 604/167.01; 604/167.03; 604/256; 604/264
(58) Field of Search ..................... 604/167, 164, 604/169, 246–249, 256, 283, 280, 264, 905, 167.01, 167.02, 167.03, 167.04, 167.05, 167.06, 164.01–164.09

(56) References Cited

U.S. PATENT DOCUMENTS

| 1,087,845 | 2/1914 | Stevens. |
| 1,103,967 | 7/1914 | Hughes. |
| 1,527,291 | 2/1925 | Zorraquin. |
| 1,867,624 | 7/1932 | Hoffman. |
| 2,485,842 | 10/1949 | Pennington ........................ 128/214 |
| 2,614,764 | 10/1952 | Annicq ................................ 242/72 |
| 2,623,521 | 12/1952 | Shaw ................................... 128/221 |
| 2,627,388 | 2/1953 | Johnson et al. .................... 251/118 |

(List continued on next page.)

FOREIGN PATENT DOCUMENTS

| 0 232 600 B1 | 4/1991 | (EP) | ............................. | A61M/1/00 |
| 575.559 | 3/1923 | (FR). | | |
| 2 308 346 | 4/1975 | (FR) | ............................. | A61B/17/34 |
| 0 405 883 A3 | 6/1990 | (GB) | ............................. | A61B/17/34 |
| 897-224 | 4/1980 | (SU). | | |
| WO 94/06506 | 3/1994 | (WO) | ............................ | A61M/39/00 |

OTHER PUBLICATIONS

Arrow International, Inc. brochure for "Arrow–Clarke™ Thoracentesis Kit with Pleura–Seal™ Valve" dated 1992.
Arrow International, Inc. brochure "Arrow–Clarke Thoracentesis Set with Pleura–Seal® Valve" dated 1994.
Sherwood Medical brochure "Introducing the Argyle® Turkel™ Safety Thoracentesis System" dated 1994.
Vernay, Custom Engineered Precision Rubber Components, Vernay Laboratories, Inc.
Surgical Laparoscopy, Mark A. Talamini, M.D. and Thomas R. Gadacz, M.D., Laparoscopic Equipment and Instrumentation, pp. 23, 40–41.
The Argyle Turkel Thoracentesis System, Sherwood Medical, 1993.
Veres Needle in the Pleural Space, Jenkins et al., pp. 1383–1385.

*Primary Examiner*—Manuel Mendez
(74) *Attorney, Agent, or Firm*—Paul E. Schaafsma; Andrew G. Rozycki; Donald O. Nickey

(57) ABSTRACT

The present invention provides a drainage catheter for the therapeutic or diagnostic aspiration of fluid or air from the thoracic or abdominal cavities. The present invention provides a catheter needle, a catheter, a needle hub, a stop cock, and a self-sealing valve. The stop cock is removably secured to the catheter by use of a Luer connection. The stop cock is additionally removably secured to the self-sealing valve, again by use of a Luer connection. Use of the Luer connection allows the catheter to be disassembled from the stop cock as well as allows the stop cock to be disassembled from the self-sealing valve. This invention allows the additional medical procedures while the catheter still remains in the patient.

12 Claims, 4 Drawing Sheets

U.S. PATENT DOCUMENTS

| | | | |
|---|---|---|---|
| 2,630,803 | 3/1953 | Baran | 128/221 |
| 2,842,124 | 7/1958 | James | 128/214 |
| 2,844,333 | 7/1958 | Davidson | 242/118.11 |
| 3,157,201 | 11/1964 | Littmann | 137/625.47 |
| 3,276,472 | 10/1966 | Jinkens et al. | 137/556 |
| 3,313,299 | 4/1967 | Spademan | 128/214.4 |
| 3,459,183 | 8/1969 | Ring et al. | 128/214.4 |
| 3,459,188 | 8/1969 | Roberts | 128/347 |
| 3,477,437 | 11/1969 | Goldberg | 128/347 |
| 3,530,492 | 9/1970 | Ferber | 128/221 |
| 3,542,026 | 11/1970 | Bledsoe | 128/278 |
| 3,547,119 | 12/1970 | Hall et al. | 128/214.4 |
| 3,557,778 | 1/1971 | Hughes | 128/2 |
| 3,703,899 | 11/1972 | Calinog | 128/347 |
| 3,713,447 | 1/1973 | Adair | 128/347 |
| 3,727,613 | 4/1973 | Sorenson et al. | 128/214.4 |
| 3,765,420 | 10/1973 | Felczak | 128/347 |
| 3,774,604 | 11/1973 | Danielsson | 128/214.4 |
| 3,830,225 | 8/1974 | Shinnick | 128/2 B |
| 3,834,372 | 9/1974 | Turney | 128/2 F |
| 3,840,008 | 10/1974 | Noiles | 128/221 |
| 3,853,127 | 12/1974 | Spademan | 128/214.4 |
| 3,875,938 | 4/1975 | Mellor | 128/214.4 |
| 3,895,632 | 7/1975 | Plowiecki | 128/214.4 |
| 3,934,576 | 1/1976 | Danielsson | 128/2.05 D |
| 3,952,729 | 4/1976 | Libman et al. | 128/2 F |
| 3,977,400 | 8/1976 | Moorehead | 128/214.4 |
| 3,990,472 | 11/1976 | Etes | 137/533.11 |
| 3,993,079 | 11/1976 | Henriques de Gatztañondo . | |
| 3,994,287 | 11/1976 | Turp et al. | 128/6 |
| 4,000,739 | 1/1977 | Stevens | 128/214.4 |
| 4,073,297 | 2/1978 | Kopp | 128/214.4 |
| 4,099,528 | 7/1978 | Sorenson et al. | 128/214.4 |
| 4,153,048 | 5/1979 | Magrini . | |
| 4,177,814 | 12/1979 | Knepshield et al. | 128/348 |
| 4,233,982 | 11/1980 | Bauer et al. | 128/347 |
| 4,245,635 | 1/1981 | Kontos | 128/214.4 |
| 4,252,122 | 2/1981 | Halvorsen | 128/349 R |
| 4,261,357 | 4/1981 | Kontos | 128/214.4 |
| 4,308,875 | 1/1982 | Young | 128/753 |
| 4,311,136 | 1/1982 | Weikl et al. | 128/214.4 |
| 4,314,565 | 2/1982 | Lee | 128/753 |
| 4,379,458 | 4/1983 | Bauer et al. | 604/264 |
| 4,403,617 | 9/1983 | Tretinyak | 128/754 |
| 4,447,235 | 5/1984 | Clarke . | |
| 4,496,348 | 1/1985 | Genese et al. | 604/167 |
| 4,511,355 | 4/1985 | Franetzki et al. . | |
| 4,531,935 | 7/1985 | Berryessa | 604/45 |
| 4,535,773 | 8/1985 | Yoon | 604/51 |
| 4,535,819 | 8/1985 | Atkinson et al. | 137/846 |
| 4,540,411 | 9/1985 | Bodicky | 604/169 |
| 4,566,480 | 1/1986 | Parham | 137/271 |
| 4,626,245 | 12/1986 | Weinstein | 604/167 |
| 4,627,841 | 12/1986 | Dorr | 604/158 |
| 4,653,475 | 3/1987 | Seike et al. | 128/4 |
| 4,655,226 | 4/1987 | Lee | 128/754 |
| 4,655,752 | 4/1987 | Honkanen et al. | 604/256 |
| 4,700,694 | 10/1987 | Shishido | 128/6 |
| 4,701,160 | 10/1987 | Lindsay et al. . | |
| 4,735,215 | 4/1988 | Goto et al. | 128/754 |
| 4,745,950 | 5/1988 | Mathieu | 137/798 |
| 4,747,840 | 5/1988 | Ladika et al. . | |
| 4,784,156 | 11/1988 | Garg . | |
| 4,808,168 | 2/1989 | Warring | 604/158 |
| 4,832,044 | 5/1989 | Garg . | |
| 4,840,184 | 6/1989 | Garg . | |
| 4,842,591 | 6/1989 | Luther | 604/283 |
| 4,844,087 | 7/1989 | Garg . | |
| 4,850,373 | 7/1989 | Zatloukal et al. | 128/749 |
| 4,850,973 | 7/1989 | Jordan et al. | 604/157 |
| 4,869,717 | 9/1989 | Adair | 604/51 |
| 4,887,998 | 12/1989 | Martin et al. | 604/110 |
| 4,891,044 | 1/1990 | Mitchell | 604/27 |
| 4,907,599 | 3/1990 | Taylor | 128/754 |
| 4,917,668 | 4/1990 | Haindl | 604/167 |
| 4,925,448 | 5/1990 | Bazaral . | |
| 4,931,042 | 6/1990 | Holmes et al. | 604/164 |
| 4,973,312 | 11/1990 | Andrew | 604/158 |
| 5,002,528 | 3/1991 | Palestrant . | |
| 5,019,096 | 5/1991 | Fox, Jr. et al. . | |
| 5,030,199 | 7/1991 | Barwick et al. | 600/29 |
| 5,030,213 | 7/1991 | Rumberger et al. . | |
| 5,035,686 | 7/1991 | Crittenden et al. . | |
| 5,036,860 | 8/1991 | Leigh et al. | 128/754 |
| 5,037,403 | 8/1991 | Garcia . | |
| 5,052,998 | 10/1991 | Zimmon . | |
| 5,057,084 | 10/1991 | Ensminger et al. | 604/167 |
| 5,059,180 | 10/1991 | McLees | 604/110 |
| 5,066,278 | 11/1991 | Hirschberg et al. . | |
| 5,069,673 | 12/1991 | Shwab . | |
| 5,078,688 | 1/1992 | Lobodzinski et al. . | |
| 5,084,034 | 1/1992 | Zanotti . | |
| 5,098,388 | 3/1992 | Kulkashi et al. | 604/158 |
| 5,098,394 | 3/1992 | Luther . | |
| 5,100,377 | 3/1992 | Freitas et al. | 604/30 |
| 5,104,381 | 4/1992 | Gresl et al. | 604/164 |
| 5,108,380 | 4/1992 | Hertlitz et al. | 604/283 |
| 5,122,122 | 6/1992 | Allgood | 604/174 |
| 5,139,485 | 8/1992 | Smith et al. | 604/158 |
| 5,154,701 | 10/1992 | Cheer et al. | 604/167 |
| 5,163,431 | 11/1992 | Griep . | |
| 5,169,387 | 12/1992 | Kronner . | |
| 5,195,980 | 3/1993 | Catlin | 604/167 |
| 5,215,527 | 6/1993 | Beck et al. . | |
| 5,226,879 | 7/1993 | Ensminger et al. | 604/93 |
| 5,300,046 | 4/1994 | Scarfone et al. . | |
| 5,300,048 | 4/1994 | Drewes, Jr. et al. . | |
| 5,308,318 | 5/1994 | Plassche, Jr. . | |
| 5,334,159 | 8/1994 | Turkel . | |
| 5,336,192 | 8/1994 | Palestrant . | |
| 5,350,360 | 9/1994 | Ensminger et al. | 604/93 |
| 5,352,198 | 10/1994 | Goldenberg et al. . | |
| 5,358,495 | 10/1994 | Lynn . | |
| 5,360,402 | 11/1994 | Conway et al. . | |
| 5,372,306 | 12/1994 | Yianilos | 239/201 |
| 5,383,259 | 1/1995 | McIntire | 24/300 |
| 5,395,350 | 3/1995 | Summers . | |
| 5,407,434 | 4/1995 | Gross . | |
| 5,423,751 | 6/1995 | Harrison et al. . | |
| 5,441,487 | 8/1995 | Vedder | 604/167 |
| 5,471,986 | 12/1995 | Ishimura et al. . | |
| 5,472,435 | 12/1995 | Sutton . | |
| 5,480,392 | 1/1996 | Mous . | |
| 5,501,227 | 3/1996 | Yock . | |
| 5,509,908 | 4/1996 | Hillstead et al. . | |
| 5,512,052 | * 4/1996 | Jesch | 604/158 |
| 5,522,400 | 6/1996 | Williams . | |
| 5,542,923 | 8/1996 | Ensminger et al. | 604/93 |
| 5,569,217 | 10/1996 | Luther . | |
| 5,575,767 | 11/1996 | Stevens . | |
| 5,593,385 | 1/1997 | Harrison et al. . | |
| 5,617,854 | 4/1997 | Munsif . | |
| 5,669,883 | * 9/1997 | Scarfone et al. | 604/167 |
| 5,743,883 | * 4/1998 | Visconti | 604/169 |

* cited by examiner

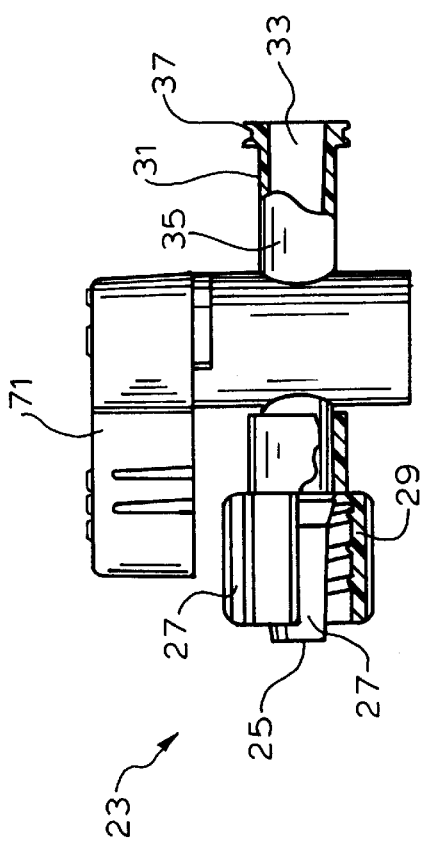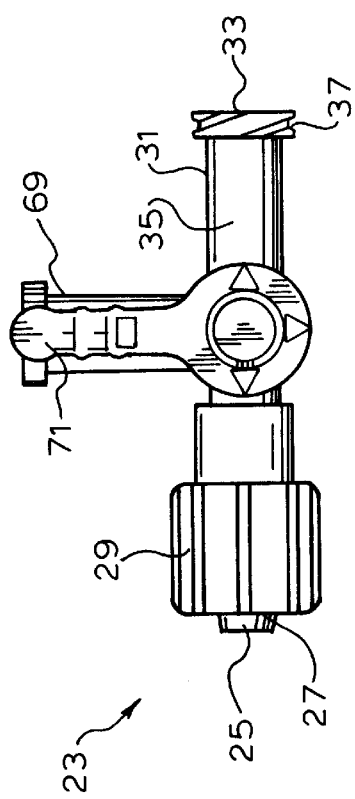

DRAINAGE CATHETER

This is related to U.S. patent application Ser. No. 08/476,609 filed on Jun. 7, 1998, now issued U.S. Pat. No. 5,743,883.

FIELD OF THE INVENTION

The present invention relates generally to catheters and in particular to a drainage catheter.

BACKGROUND OF THE INVENTION

Use of devices for the therapeutic or diagnostic aspiration of fluid or air from the thoracic or abdominal cavities is known in the art. The aspiration of fluid or air from the thoracic or abdominal cavities is desirable in relieving symptoms caused by fluid or air build up in such cavities. Drainage catheters are also used to supply physicians with samples from the thoracic or abdominal cavities for analysis. Generally, drainage catheters employ a catheter needle, a needle hub, a stop cock, and a self-sealing valve. The catheter is permanently bonded to the stop cock, and the stop cock is permanently bonded to the self-sealing valve.

Devices of the prior art, however, are not suitable for use as a long-term drainage catheters because of the weight and bulk of the device. Thus, physicians are required to use multiple drainage catheters because of the failure of prior devices to act as long-term drainage devices.

What would thus be advantageous would be to provide a catheter which was suitable for use for the therapeutic or diagnostic aspiration of fluid or air from the thoracic or abdominal cavities. The device would additionally be capable of use as a long term drainage catheter. Such a design would achieve the advantages without significantly adding cost.

SUMMARY OF THE INVENTION

The present invention provides a drainage catheter for the therapeutic or diagnostic aspiration of fluid or air from the thoracic or abdominal cavities. The present invention can be used as a long-term drainage catheter. The present invention does so without adding appreciably to the cost of the prior art devices.

The present invention provides a catheter needle, a catheter, a needle hub, a stop cock, and a self-sealing valve. The stop cock is removably secured to the catheter by use of a Luer connection. The stop cock is additionally removably secured to the self-sealing valve, again by use of a Luer connection. Use of the Luer connection allows the catheter to be disassembled from the stop cock as well as allows the stop cock to be disassembled from the self-sealing valve.

The catheter needle can be inserted into the patient to perform therapeutic or diagnostic aspiration of fluid or air from the thoracic or abdominal cavities. Upon completion of this procedure, the catheter can be disassembled and can be used as a long term drainage catheter. Thus, the present invention can be used with other medical equipment, such as a house vacuum, any drainage system, syringe, or valve, for use with additional medical procedures within the thoracic or abdominal cavities by simply connecting such medical equipment to the standard Luer lock provided on the catheter.

BRIEF DESCRIPTION OF THE DRAWINGS

FIG. 3 is a partially cut-away view of the stop cock of the drainage catheter of FIG. 1.

DETAILED DESCRIPTION OF A PREFERRED EMBODIMENT

Figure 1:
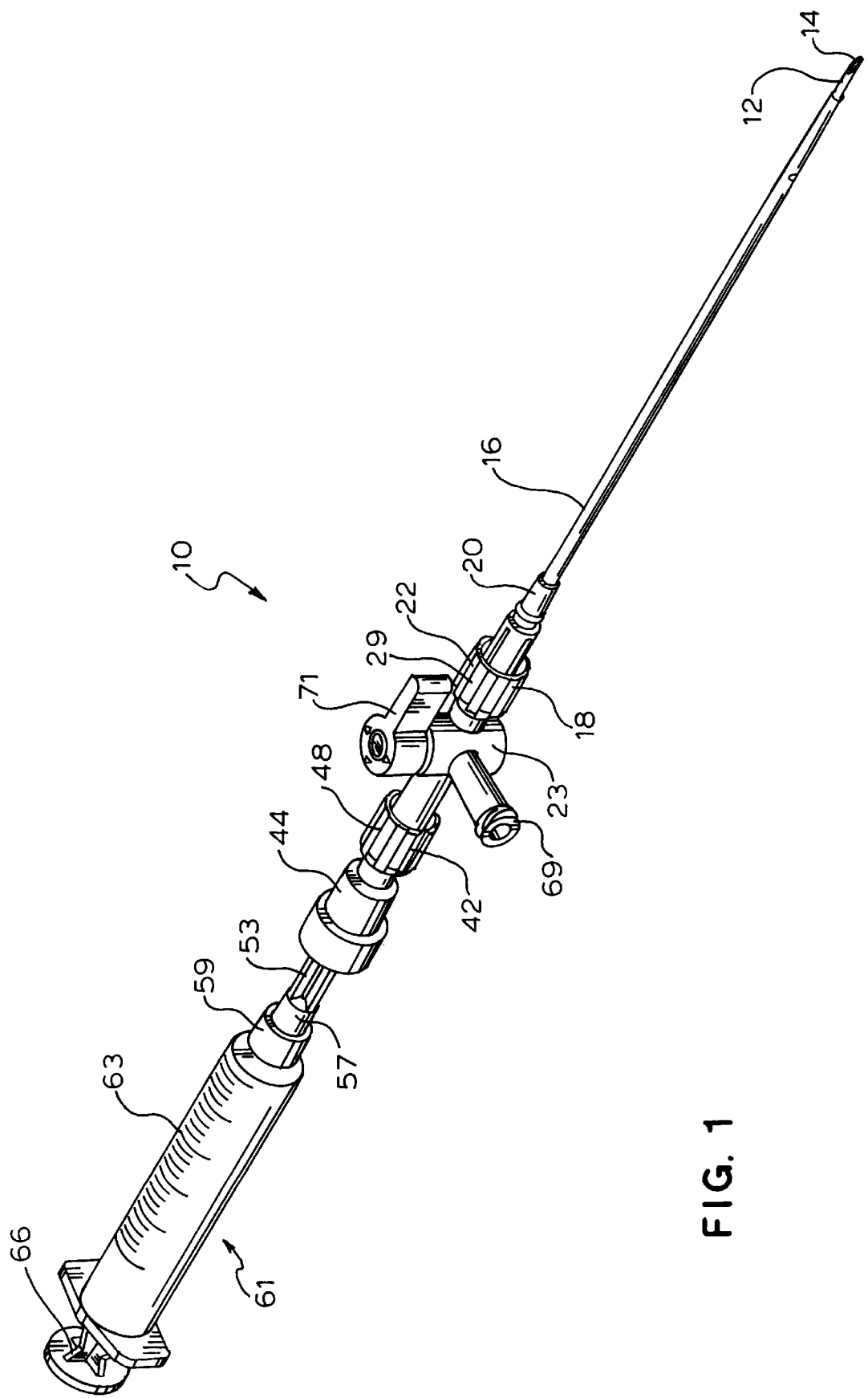
FIG. 1 is a perspective view of a drainage catheter device made in accordance with the principles of the present invention.
Figure 2:
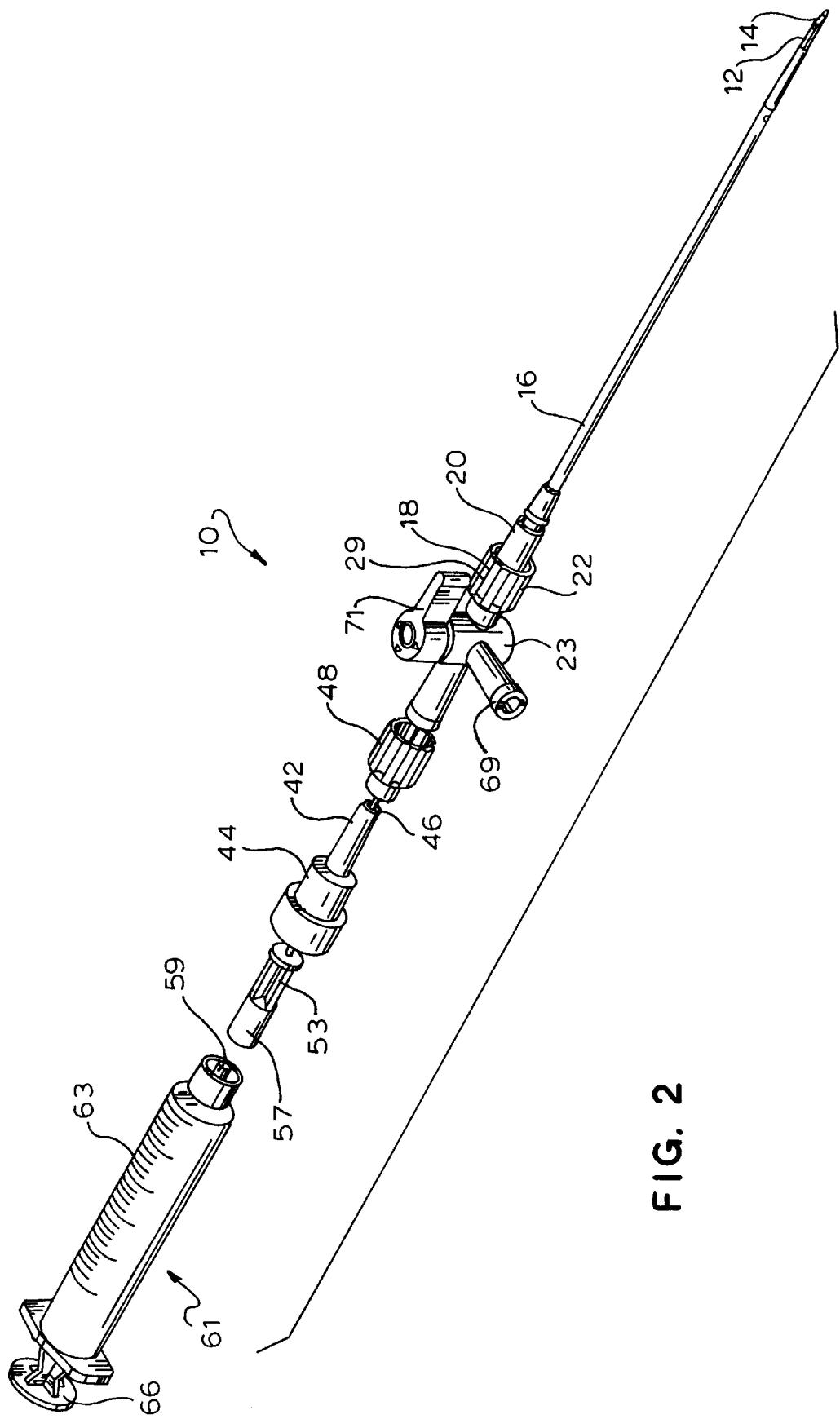
FIG. 2 is a perspective view of the drainage catheter of FIG. 1 in a partially exploded view.

Referring first to FIGS. 1 and 2, perspective views of a drainage catheter 10 made in accordance with the principles of the present invention is seen. The drainage catheter 10 includes a catheter needle 12. The catheter needle 12 is preferably a sixteen gauge, eighteen gauge or twenty-two gauge needle. The length of the catheter needle 12 is sufficient to reach the pleural cavity. The catheter needle 12 is preferably made from a 304 gauge stainless steel. The catheter needle tip 14 is preferably formed by use of a double-needle grind. Thus, the catheter needle tip 14 is preferably made by first grinding the needle tip to a first edge at approximately 13 to 17 degrees, and then grinding a second edge of the needle tip at an angle of approximately 25 to 29 degrees.

A catheter 16 is provided over the catheter needle 12. The catheter 16 is preferably 5 to 8 FR. The catheter 16 is preferably made of polyurethane. The length of the catheter 16 is preferably 6.35 cm. (2.5 in.) or 12.19 cm.(4.8 in.). The catheter 16 can be coated with a friction reducing substance such as a hydrophillic (silicone or Teflon PTFE) coating.

At the end of the catheter 16 opposite the catheter needle tip 14, a Luer connector 18 is provided. The Luer connector 18 includes housing 20 which defines a female Luer cavity. The outer surface of the female Luer housing defines a threaded bolt portion for threaded engagement with a male Luer connector.

A Luer connector 25 is defined on one end of a stop cock 23. The Luer connector 25 includes a protruding male Luer member 27 surrounded by a threaded nut member 29. Thus, the catheter 16 can be removably secured to the stop cock 23 by mating the female Luer cavity and the male Luer member 27 and threadingly engaging the Luer connector 18.

At the end of the stop cock 23 opposite the male Luer 25, a Luer member 31 is provided. A female Luer cavity 33 is defined in housing 35, the outer surface of which defines a threaded bolt portion 37 for threadingly engaging a male Luer member 42. A male Luer connector 42 is defined on one end of a self-sealing valve 44. The male Luer connector 42 includes a protruding male member 46 surrounded by a threaded nut member 48. Thus, the stop cock 23 can be removably secured to the self sealing valve 44 by mating the female Luer cavity 33 and the male Luer member 46 and threadingly engaging the Luer connector 42.

Contained on the end of the self-sealing valve 44 opposite the male Luer connector 42 is a needle hub 53. The needle hub 53 is designed for an ergonomic fit for the health care professional during use. The needle hub 53 defines a Luer connector 55. The Luer connector 55 includes a female Luer cavity defined in housing 57. The outer surface of the housing 57 defines a bayonet portion for locking engagement with a male Luer connector 59. A male Luer connector 59 is provided in a syringe 61 which can be removably secured to the needle hub 53 by mating the female Luer cavity with the male Luer member 59 and threadingly engaging the Luer lock connector 55. The syringe 61 includes a cylindrical fluid retaining cavity 63 which extends rearwardly from the male Luer connector 59. Contained in the cylindrical cavity 63 is a plunger 66.

Referring now to FIG. 3, a cross-sectional view of the stop cock 23 is seen. The stop cock 23 includes the female Luer cavity 33 defined in housing 35. The exterior of the housing 35 further defines a threaded nut member 29 for threadingly engaging the Luer connector 42 of the self-sealing valve 44. The female Luer cavity 33 defines the first outflow position of the stop cock 23. Contained on the opposite end of the stop cock 23 is a Luer connector 25. The Luer connector 25 includes a protruding male Luer member 27 which is surrounded by a threaded nut member 29 for threadingly engaging the Luer connector 18 of the catheter 16. The male Luer member 27 defines the inflow of the stop cock 23.

The second outflow is defined by a side port 69 of the stop cock 23. The side port 69 extends perpendicularly to an axis defined by the inflow and first outflow. A stop cock handle 71 is provided. The position of the stop cock handle 71 controls the direction of the flow of fluid within the stop cock 23. The stop cock handle 71 is movable from a first position, where the flow of fluid through the stop cock 23 is closed, to a second position, where the flow of fluid through the first outflow is allowed. When the stop cock handle 71 is placed in a third position, flow is allowed from the inflow to the second outflow.

Figure 4:
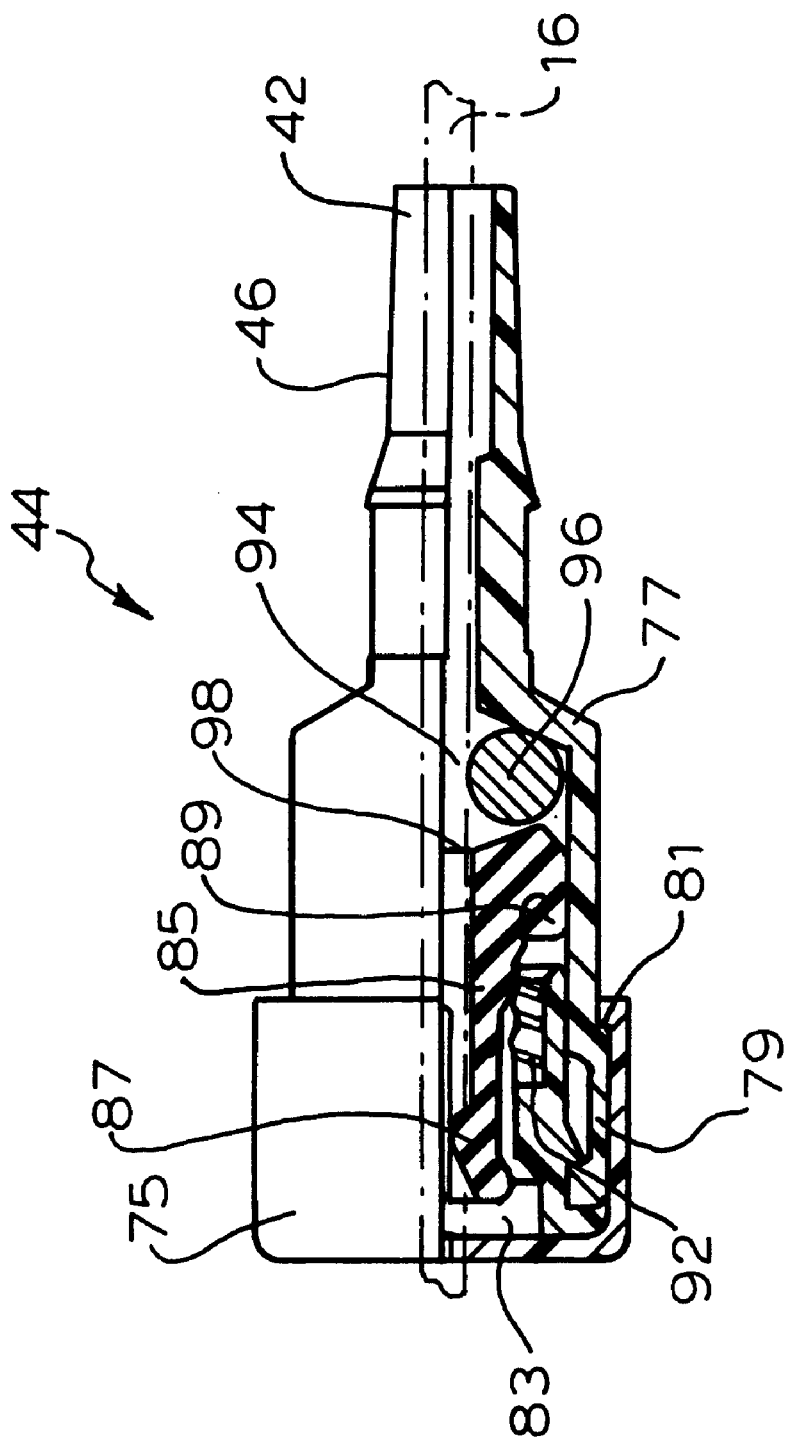
FIG. 4 is a cross-sectional view of the self-sealing valve of the drainage catheter of FIG. 1.

Referring now to FIG. 4, a partial sectional view of the self-sealing valve 44 is seen. Contained on a first end of the self-sealing valve 44 is a male Luer member 46. Extending rearwardly from the male Luer member 46 is a first valve housing 75. A second valve housing 77 is also provided. The first valve housing 75 engages the second valve housing by a pair of bayonetted locking members 79 extending rearwardly which engage a groove 81 defined on the second valve housing 77. When engaged together, the valve housing 75, 77 defines a housing cavity 83.

Captured within the housing cavity 83 is a plunger 85. The plunger 85 includes a front protruding member 87 behind which extends a seating member 89. The plunger 85 further defines a through way extending along the axis of the plunger 85. The plunger 85 carries a spring 92 which provides bias to the plunger 85 when captured in the valve housing 75,77. The spring 92 is preferably made of 302 grade stainless steel and is designed to provide approximately 1605 g per cm. (8.98 lbs per in.) of force.

Contained in the valve housing 75, 77 is a ball cavity 94. The ball cavity 94 defines a seat 98 over the plunger throughway. Contained within the ball cavity 94 is a ball bearing 96. The ball bearing 96 is preferably made from 302 grade stainless steel. When the catheter needle 12 extends through the self-sealing valve 44, the ball bearing 96 is forced to the side, off of the seat 98, which biases the spring 92 and thus cocks the plunger 85 into the open position. When the catheter needle 12 is removed from the self-sealing valve 44, the spring 92 biases the plunger 85 forward which secures the ball bearing 96 against the seat 98 over the plunger throughway and the male Luer passage.

In use, the drainage catheter 10 is held by the health care professional by grasping the stop cock 23 with the sharp needle tip 14 extending beyond the catheter 16. The skin is punctured by the catheter needle 12 and catheter 16, and the catheter assembly is introduced into the patient. The catheter assembly is advanced into the patient until fluid can be aspirated through the catheter needle 12 into the syringe 61. The catheter needle 12 is then withdrawn, thus retaining the catheter 16 in the patient. Fluid samples can then be withdrawn from the side port 69 of the stop cock 23 and by withdrawing the plunger 66 of the syringe 61.

The self-sealing valve 44 is designed to prohibit the catheter needle 12 from being reinserted into the drainage catheter 10 after it has been withdrawn. Upon removal of the catheter needle 12, the plunger 85 is biased forward which secures the ball bearing 96 against the seat 98, over the plunger 85 throughway and the male Luer 46. This precludes reinsertion of the catheter needle 12.

After completion of the therapeutic or diagnostic aspiration of fluid, the health care professional can maintain the drainage catheter 10 in the thoracic or abdominal cavities and utilize the drainage catheter 10 for additional procedures. This is done by disconnecting the Luer connection between the self-sealing valve 44 and the stop cock 23, and removing the self-sealing valve 44. In this arrangement a Luer connection to the catheter 16 is available through the stop cock 23. Alternatively, the health care professional can maintain the drainage catheter 10 in the thoracic or abdominal cavities and remove both the self-sealing valve 44 and the stop cock 23 by disengaging the Luer connection between the stop cock 23 and the catheter 16. In this arrangement, a Luer connection directly with the catheter 16 is available.

It should be understood that various changes and modifications preferred in to the embodiment described herein will be apparent to those skilled in the art. For example, while depicted herein as straight, the catheter can be of any appropriate shape, such as a J shape made of memory steel. As a further example, the catheter can be provided in a direct Luer engagement with the self-sealing valve. Such changes and modifications can be made without departing from the spirit and scope of the present invention and without demising its attendance advantages. It is therefore intended that such changes and modifications be covered by the appended claims.

What is claimed is:

1. A catheter assembly, comprising:
   a catheter;
   a needle removably contained within the catheter;
   a first valve secured to the catheter; and
   a self-sealing valve secured to the first valve;
   the first valve being removably secured to the catheter, the first valve being additionally removably secured to the self-sealing valve;
   whereby the catheter can be disassembled from the first valve and the first valve can be disassembled from the self-sealing valve.

2. The catheter assembly of claim 1, further wherein the first valve is removable secured by a Luer connection.

3. The catheter assembly of claim 1, further wherein the self-sealing valve is removably secured by a Luer connection.

4. The catheter assembly of claim 1, wherein the self-sealing valve comprises a biased ball check valve.

5. The catheter assembly of claim 1, wherein the first valve comprises a three way valve.

6. The catheter assembly of claim 5, wherein the three way valve is a stop cock.

7. A catheter assembly, comprising:
   a catheter comprising a Luer connection;
   a needle removably contained with the catheter; and
   a sealing valve comprising a Luer connection, the Luer connection of the self-sealing valve cooperating with the Luer connection of the catheter to removably secure the self-sealing valve to the catheter;
   whereby the catheter can be dissembled from the self-sealing valve.

8. The catheter assembly of claim 2, wherein the self-sealing valve comprises a biased ball check valve.

9. The catheter assembly of claim 2, further including a first valve removably secured to the catheter and to the self-sealing valve.

10. The catheter assembly of claim 9, further wherein the first valve is removably secured by a Luer connection.

11. The catheter assembly of claim 9, wherein the first valve comprises a three way valve.

12. The catheter assembly of claim 11, wherein the three way valve is a stop cock.

\* \* \* \* \*